(12) United States Patent
Vetter et al.

(10) Patent No.: US 6,912,800 B2
(45) Date of Patent: Jul. 5, 2005

(54) AUTOCLAVING PREFILLED SYRINGES

(75) Inventors: Udo J. Vetter, Ravensburg (DE);
Friedrich Treuer, Ravensburg (DE);
Klaus Steigenberger, Wangen (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 0 days.

(21) Appl. No.: 10/622,439

(22) Filed: Jul. 18, 2003

(65) Prior Publication Data

US 2004/0078993 A1 Apr. 29, 2004

(30) Foreign Application Priority Data

Aug. 3, 2002 (DE) .......................................... 102 35 542

(51) Int. Cl.[7] .................................................. F26B 5/04
(52) U.S. Cl. ............................. 34/380; 34/413; 34/209; 422/302
(58) Field of Search .......................... 34/380, 391, 413; 34/201, 209, 239; 422/302, 307

(56) References Cited

U.S. PATENT DOCUMENTS

| | | | | |
|---|---|---|---|---|
| 4,576,792 A | * | 3/1986 | Martensson | 422/27 |
| 5,439,643 A | * | 8/1995 | Liebert | 422/25 |
| 5,842,326 A | * | 12/1998 | Wolf | 53/425 |
| 6,394,977 B1 | * | 5/2002 | Taylor et al. | 604/100.03 |
| 6,422,084 B1 | * | 7/2002 | Fernald et al. | 73/705 |

* cited by examiner

Primary Examiner—Stephen Gravini
(74) Attorney, Agent, or Firm—Herbert Dubno; Andrew Wilford

(57) ABSTRACT

A container which is to be autoclaved has a shiftable plunger that defines a compartment filled with a fluid. The container is confined in a pressurizable chamber and heated so as to change a pressure in the compartment of the container. The pressure in the compartment of the container is monitored and an output corresponding thereto is generated. Pressure in the chamber around the container is continuously varied so as to be generally equal to the instantaneous monitored pressure in the compartment of the container. In this manner the plunger is not moved by thermal expansion or contraction of the fluid.

17 Claims, 2 Drawing Sheets

AUTOCLAVING PREFILLED SYRINGES

FIELD OF THE INVENTION

The present invention relates to a method of and apparatus for autoclaving prefilled syringes and the like. More particularly this invention concerns such an autoclaving method where the prefilled syringes are subjected to superatmospheric pressure and heat during the sterilization operation.

BACKGROUND OF THE INVENTION

It is standard to sterilize containers such as prefilled syringes having plungers in an autoclave that forms a pressurizable chamber around the containers being sterilized and that is pressurized with hot air and/or saturated steam. The chamber is maintained at a superatmospheric pressure of about 1.1 bar and the containers are heated to about 120° C. for 20 to 60 minutes to kill any bacteria.

As the syringes are being brought from room temperature to the desired high autoclave temperature, the contents, typically both liquid and gas, expand somewhat. This can have the deleterious consequence of moving the plunger from its starting position. When the syringes are subsequently cooled, static friction normally prevents the contracting gas/liquid contents from pulling the plunger back to the starting position.

This displacement of the plunger has several disadvantages. First of all, if the contents of the syringe are left under subatmospheric pressure, it is possible that the syringe will draw in nonsterile air, contaminating its contents prior to use. Furthermore when the syringes are to be fitted with plunger stems after autoclaving, the machine that mounts the plunger stems, which project rearward out of the syringe body, can damage the plunger, stem, and/or syringe body since the plunger will not be in the position the stem-installing device is set for.

Hence it is known to control the pressurization of the autoclave by means of a computer program that takes into account the composition of the contents of syringes and their coefficients of thermal expansion. This program is used to increase the pressure in the autoclave around the syringes as they are heated, with the aim of maintaining the pressure inside the syringes the same as the pressure outside so that the plungers do not shift. Similarly as the containers being autoclaved cool down, the program reduces the autoclave pressure, thereby also preventing the plungers from shifting.

Such a solution is technically very complex. As the composition of the liquid in the syringes changes, the program must be corrected, as different liquids volatilize at different temperatures and to different extents. Similarly different plungers and syringe bodies have different coefficients of frictions, requiring more or less sensitivity in the calculation. Hence it is necessary to reprogram each time the syringe contents being autoclaved changes, and it is absolutely impossible to simultaneously autoclave syringes holding different substances. What is more, different syringes conduct heat differently and the contents of the syringes have different heat capacities and abilities to conduct heat, further complicating calculation of the pressure/temperature curve.

The result is that programming the increase and decrease in pressure in the autoclave is a hit and miss operation, typically done more empirically or experimentally than in accordance with any manageable algorithm. What is more, within a given batch of syringes it is possible for there to be some variation as to air content and the like. The result is that under the best of circumstances, one can count on the plungers moving somewhat. Even when the plungers end up in the starting position, if they have moved significantly, the result can be deposits of the medicament between the plunger and the inner side walls of the syringe or even on exposed inner surfaces of the syringe.

OBJECTS OF THE INVENTION

It is therefore an object of the present invention to provide an improved system for autoclaving a container having a plunger defining a compartment filled with liquid and/or gas.

Another object is the provision of such an improved system for autoclaving a container having a plunger defining a compartment filled with liquid and/or gas which overcomes the above-given disadvantages, that is which ensures that the plunger does not move significantly, regardless of the contents or constructions of the container.

SUMMARY OF THE INVENTION

A method of autoclaving a container in which a shiftable plunger defines a compartment filled with a fluid. The container is confined in a pressurizable chamber and heated so as to change a pressure in the compartment of the container. The pressure in the compartment of the container is monitored and an output corresponding thereto is generated. Pressure in the chamber around the container is varied so as to be generally equal to the instantaneous monitored pressure in the compartment of the container.

Thus according to the instant invention there is no need to calculate coefficients of thermal expansion and the like. Instead the actual pressure inside the container, normally a syringe, is itself monitored. There can be no translation or calculation error; instead the exact parameter that is in question is the one being monitored. This takes the composition of the fluid(s) in the container, the conductivity of the container, and the like out of the equation.

According to the invention the pressure is monitored by monitoring movement of the plunger as the container is heated. More particularly a pair of light curtains are provided flanking the plunger. The pressure in the chamber is increased when the plunger moves across one of the light curtains and is decreased when the plunger moves across the other of the light curtains. Alternately, the pressure is monitored by detecting the distance between the plunger and a fixed sensor. This can be done optically or by ultrasound. When done optically, the distance is detected by means of reflection, e.g. of an angled mirror attached to the plunger, or by the Doppler effect.

In accordance with the invention the pressure is monitored by providing a pressure sensor exposed to the fluid in the container. Such a sensor can extend through a wall of the container or, when the container is a syringe, through a tip cap thereof.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
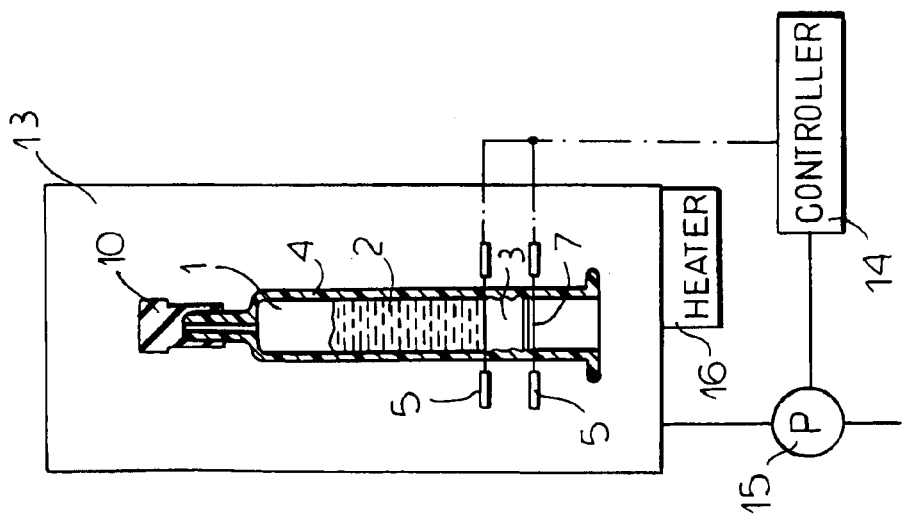
FIG. 1 is a largely schematic view partly in axial section through an apparatus for carrying out the method of this invention.

As seen in FIG. 1 a container 4, here a cylindrical syringe body with a tip cap 10 and a plunger 3, is filled with a body of liquid 2 and gas 1. To sterilize the contents comprised of the gas 1 and liquid 2, the syringe 4, normally with a plurality of other such containers, is put in an autoclave chamber 13 associated with a heater 16, normally that injects steam into it, and a pump 15 that maintains it at superatmospheric pressure. This pump 15 can in fact be constituted by a pressure-control valve through which high-pressure superheated steam is fed into the chamber 13.

According to the invention the position of the plunger 3 is monitored by a pair of sensors 5 constituted as light curtains with light beams 7. They are connected to a controller 14 that operates the pump 15. Thus when pressure inside the syringe 4 increases up due to thermal expansion caused by heating, the plunger 3 will move outward (down in FIG. 1) slightly and interrupt the outer light curtain 5. This will be transmitted as an overpressure signal to the controller 14 which will operate the pump 15 to increase pressure inside the chamber 13 until the plunger 13 moves back between the light curtains 5, to its starting position.

When, on cooling, the plunger 3 moves oppositely inward to break the beam 7 of the inner light curtain 5, an underpressure signal is sent to the controller 14 which allows the pump 15 to reduce pressure in the chamber 13 until the plunger 3 is back in its starting position. Regardless of the composition of the gas 1 and liquid 2, this system will ensure is that the plunger 3 ends up in its starting position and, in fact, that it will not move significantly out of this position during processing.

Figure 3:
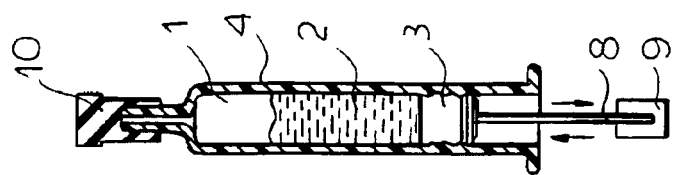
FIGS. 2 through 6 are axial sections through details of variants on the system of the present invention.
Figure 2:
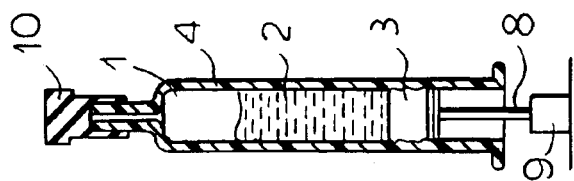

FIG. 2 shows a variation on the system where the plunger 3 is provided with a stem 8 connected to an ultrasound position detector 9 that in turn is connected to the controller 14. In FIG. 3 the position detector 9 operates optically.

Figure 6:
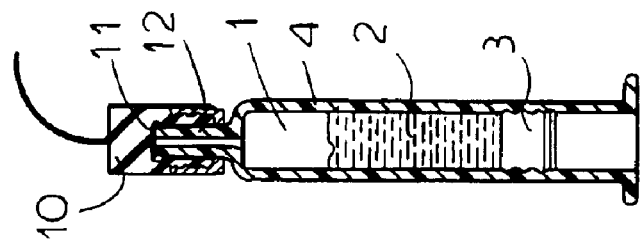
Figure 5:
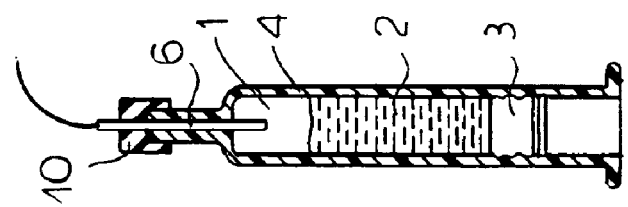
Figure 4:
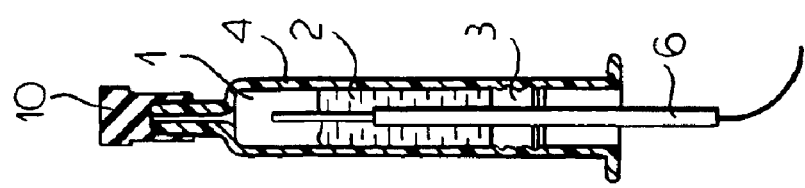

FIG. 4 has a pressure sensor 6 that extends through the plunger 3 into the air space 1 of the syringe 4, while in FIG. 5 it extends through the tip cap 10. FIG. 6 shows a sensor 11 fitted over the tip 12 of the syringe 4 to measure the pressure therein.

Thus in FIGS. 4 through 6 the pressure in the container 4 is monitored directly, whereas in FIGS. 1 through 3 it is monitored by detecting the position of the plunger 3.

We claim:

1. A method of autoclaving a container in which a shiftable plunger defines a compartment filled with a fluid, the method comprising the step of:
   confining the container in a pressurizable chamber;
   heating the container in the chamber and thereby changing a pressure in the compartment of the container;
   monitoring the pressure inside the container in the compartment thereof and generating an output corresponding thereto; and
   varying pressure in the chamber outside the container so as to be generally equal to the monitored pressure inside the container in the compartment thereof.

2. The autoclaving method defined in claim 1 wherein the pressure is monitored by monitoring movement of the plunger as the container is heated.

3. The autoclaving method defined in claim 2 wherein the pressure is monitored by a pair of light curtains flanking the plunger, the pressure in the chamber being increased when the plunger moves across one of the light curtains and decreased when the plunger moves across the other of the light curtains.

4. The autoclaving method defined in claim 2 wherein the pressure is monitored by detecting the distance between the plunger and a fixed sensor.

5. The autoclaving method defined in claim 4 wherein the distance is detected optically or by ultrasound.

6. The autoclaving method defined in claim 5 wherein the distance is detected optically by means of reflection or the Doppler effect.

7. The autoclaving method defined in claim 1 wherein the pressure is monitored by providing a pressure sensor exposed to the fluid in the container.

8. An apparatus for autoclaving a container in which a shiftable plunger defines a compartment filled with a fluid, the apparatus comprising:
   a pressurizable chamber in which the container is confined;
   pump means for pressurizing the chamber;
   means for heating the container in the chamber and thereby changing a pressure inside the container in the compartment thereof;
   means including a sensor for monitoring the pressure inside the container in the compartment thereof and generating an output corresponding thereto; and
   control means connected to the sensor and to the pump means for a varying pressure in the chamber outside the container so as to be generally equal to the monitored pressure inside the container in the compartment thereof.

9. The autoclaving apparatus defined in claim 8 wherein the sensor monitors movement of the plunger as the container is heated.

10. The autoclaving apparatus defined in claim 9 wherein the sensor includes a pair of light curtains flanking the plunger, the control means increasing pressure in the chamber when the plunger moves across one of the light curtains and decreasing it when the plunger moves across the other of the light curtains.

11. The autoclaving apparatus defined in claim 9 wherein the sensor detects the distance between the plunger and a fixed sensor.

12. The autoclaving apparatus defined in claim 8 wherein the sensor operates optically or by ultrasound.

13. The autoclaving apparatus defined in claim 12 wherein the sensor operates optically by means of reflection or the Doppler effect.

14. The autoclaving apparatus defined in claim 8 wherein the sensor is exposed to the fluid in the container.

15. The autoclaving apparatus defined in claim 14 wherein the container has a wall and the sensor projects through the wall.

16. The autoclaving apparatus defined in claim 14 wherein the container is a syringe having a tip cap and the sensor projects through the tip cap.

17. The autoclaving apparatus defined in claim 1 wherein the pressure in the chamber is varied continuously in accordance with the output.

* * * * *